United States Patent
Itoh et al.

(10) Patent No.: US 6,248,732 B1
(45) Date of Patent: Jun. 19, 2001

(54) OPHTHALMOLOGICAL COMPOSITION COMPRISING ACTIVATED VITAMIN D

(75) Inventors: Seiji Itoh, Mobara; Yasuo Ishii, Kawaguchi; Katsuhiko Mukai, Kashiwa, all of (JP)

(73) Assignee: Katsuhiko Mukai, Kashiwa (JP)

( * ) Notice: Subject to any disclaimer, the term of this patent is extended or adjusted under 35 U.S.C. 154(b) by 0 days.

(21) Appl. No.: 08/913,522

(22) PCT Filed: Mar. 18, 1996

(86) PCT No.: PCT/JP96/00697

§ 371 Date: Nov. 24, 1997

§ 102(e) Date: Nov. 24, 1997

(87) PCT Pub. No.: WO96/29079

PCT Pub. Date: Sep. 26, 1996

(30) Foreign Application Priority Data

Mar. 20, 1995 (JP) ........................................ 7-60321

(51) Int. Cl.⁷ ........................... A61K 31/59; A61K 31/34
(52) U.S. Cl. ........................... 514/167; 514/168; 514/474; 514/912
(58) Field of Search ..................... 514/474, 167, 514/168, 912, 913

(56) References Cited

FOREIGN PATENT DOCUMENTS

WO 94/01398   1/1994   (WO).
WO 94/04143   3/1994   (WO).

OTHER PUBLICATIONS

G. Conte, et al., Biosciences Information Service, 1 page, "Ocular Findings in a Case of Pseudohypoparathyroidism," 1987 (English Abstract Only).

H. R. Koch, Medizinische Klinik, pps. 2152–2162, "Katarakte Bei Allgemeinerkrankungen (Cataracts in the Course of General Disease)," 1976.

L. Leclerc, et al., Revue Francaise d'Endocrinologie Clinique—Nutrition Et Metabolisme, vol. 26, No. 1, pps. 59–63, "Hypercalcémie Médicamenteuse Au Cours Du Traitement De La Cataracte (Drug–Induced Hypercalcemia During Treatment for Cataract)," 1985.

Derwent Publications, AN 1976–84227X, JP 51 108046, Sep. 25, 1976.

Derwent Publications, AN 1977–89037Y, JP 52 130905, Nov. 2, 1977.

*Primary Examiner*—Zohreh Fay
(74) *Attorney, Agent, or Firm*—Oblon, Spivak, McClelland, Maier & Neustadt, P.C.

(57) ABSTRACT

An ophthalmic composition comprises active vitamin D as an effective component and is used for preventing deterioration of the optical transparency, occurrence of high intraocular pressure diseases or defective sight, observed after an ophthalmic operation, due to hyperplasia of the anterior ocular cells in the tissues damaged by the ophthalmic operation, which are in course of a healing process, and/or excess production of cellular materials.

The ophthalmic composition can be dropped in the eye after operations such as those for cataract, for transplantation of intraocular lenses and for cornea to maintain the intraocular transparency of the anterior ocular region, to control the hyperplasia of the anterior ocular cells in the tissues damaged by the ophthalmic operation, which are in course of a healing process, and/or excess production of cellular materials and to thus prevent any reduction of visual acuity.

14 Claims, No Drawings

OPHTHALMOLOGICAL COMPOSITION COMPRISING ACTIVATED VITAMIN D

This application is a 371 of PCT/JP96/0069 filed on Mar. 18, 1996.

TECHNICAL FIELD

The present invention relates to an ophthalmic composition and more specifically to an ophthalmic composition for treating patients suffering from intraocular inflammation, glaucoma and corneal degeneracy and for preventing any occurrence of hyperplasia of anterior ocular cells during the damaged tissue-healing process after operations thereof and/or for preventing, for instance, any reduction in transparency, any change in refractive power and any increase in intraocular pressure.

2. Prior Art

Rachitis is one of the osteopathy, and it has formerly been believed that the rachitis is closely related to the action of the sunlight. Thereafter, however, it has been found out that a certain vitamin is closely involved in the rachitis. This anti-rachitis vitamin is named vitamin D. Vitamin $D_2$ obtained by purifying vitamin $D_1$ which is a mixture with other isomers as well as vitamin $D_3$ discovered through the subsequent studies have widely been used in the treatments of many patients suffering from osteopathy such as rachitis, osteomalacia, osteoporosis, ostitis fibrous and osteosclerosis, malignant tumors such as breast cancer and carcinoma of large intestine, as well as dermatosis such as psoriasis. Vitamin D is an essential vitamin for the bone modeling and it is prescribed by the Ministry of Public Welfare of Japan that the required amount of this nutrient to be taken with foods is set at 200 IU (5 µg)/day. However, the required amount of the nutrient differs from that prescribed in foreign countries (i.e., 400 IU/day) because of the presence of vitamin $D_3$ which is produced in the skin by the action of ultraviolet light rays through sunbathing. In other words, it is necessary to take excess of vitamin D in case where sufficient sunbathing is not ensured. Vitamins $D_2$ to $D_7$ are classified as vitamins having rachitis-inhibitory activity, but presently used in the treatment of this disease are vitamin $D_2$ and vitamin $D_3$ having high physiological activity.

Vitamin D's are administered to patients per oral route or by injection. In case of skin diseases, they are also administered in the form of ointments. it has been known that the vitamin D undergoes a change in its molecular structure through the action of ultraviolet rays or in the liver and kidney and that it is thus converted into active vitamin D having high biological activities. It has been recognized that vitamin D's have not only calcium-regulatory effect, but also other biological activities since the discovery of the active vitamin $D_3$, i.e., calcitriol (1α,25-dihydroxy cholecalciferol) as a derivative of the cholecalciferol. As other derivatives or analogues of the cholecalciferol, there have been known, for instance, alpha-calcidol (1α-monohydroxy cholecalciferol) and calcifedol (25-monohydroxy cholecalciferol). There have recently been known about 16 kinds of cholecalciferol derivatives. In addition, there have been developed several kinds of cholecalciferol analogues such as OCT (2-oxacalcitriol) and calcipotriol. The presence of active vitamin D receptors in cells have been discovered and there have been conducted studies on inhibition of cellular activities because of the ability of the active vitamin D's to control the production of various cytokines.

In the field of the ophthalmology, it has been known, as the symptoms caused due to vitamin deficiency, for instance, night blindness, Bitot's spots on conjunctiva, and xerophthalmia due to vitamin A deficiency; beriberi and weak eyesight because of vitamin $B_1$ deficiency; superficial punctate keratitis because of the vitamin $B_2$ deficiency (sometimes associated with retroocular neuropapillitis and optic atrophy); scorbutus due to the vitamin C deficiency (wherein there are often observed bleeding in eyelids, conjunctivae and retinae)

Dr. Ohashi et al. in Osaka University studied the inhibitory effect of vitamin $D_3$ against the expression of MHC class antigens in order to suppress any rejection observed during the keratoplasty and suggest that vitamin $D_3$ may serve to control the rejection of the transplantation of cornea (Bulletin of Ophthalmologic Society in Japan, 1990, Vol. 94, an extra edition, p. 250).

Japanese Un-Examined Patent Publication No. Hei 3-24016 discloses studies of cultivation of human glia cells wherein the ability of active vitamin $D_3$ to inhibit the proliferation of glia cells and also suggests that active vitamin $D_3$ may be applied to the treatment of patients suffering from proliferative retinopathy.

Japanese Examined Patent Publication No. Hei 4-43887 discloses that active vitamin $D_3$ is effective for the treatment of cataract such as congenital cataract, senile cataract, complicated cataract and diabetic cataract.

U.S. Pat. No. 5,254,538 discloses that vitamin D compounds are effective in healing of wounds and healing of a variety of ulcers.

The surgical operation with a scalpel has been employed for the correction of shortsightedness and astigmatisms, but this would adversely affect the visual power. For instance, the operated eye proceeds to the over correction after the operation and the incised site of the cornea becomes turbid or causes irregular reflection, which impair the visual acuity.

As laser device for operating cornea, there have been known an excimer laser and an Ho:YAG laser. The laser operations for cornea are divided into the operations for healing diseases and those for correcting the visual power.

Glaucoma is a disease in which a high intraocular pressure disease is caused due to excess production of the aqueous humor through the posterior chamber gonion or a trouble of flow paths for the aqueous humor in the anterior chamber gonion because of a certain intraocular disease and this leads to the visual field defect. Alternatively, the high intraocular pressure disease may sometimes be caused by a simple mechanical trouble of the flow paths for the aqueous humor in the anterior chamber gonion.

Corneal degeneracy (corneal dystrophy) is a disease in which heterogeneous proteins are mainly deposited on keratocytes due to the dysbolism of the corneal epithelial cells or keratocytes and this in turn leads to corneal haze/opacity. Examples of such corneal degeneracy include granular corneal degeneracy, porphyritic corneal degeneracy, cancellated corneal degeneracy, colloidal guttate corneal degeneracy, Schneider's corneal degeneracy and Francois' corneal degeneracy. On the other hand, corneal ulcer is a disease in which a collagenase is excessively produced by the corneal epithelial cells to thus form an ulcer. Accordingly, the corneal degeneracy and the corneal ulcer are quite different from one another in the etiological causes and clinical findings.

In a patient who has been subjected to an operation for incising the cornea using an excimer laser, there is observed, after the operation, the occurrence of hyperplasia of the cells at the inflamed corneal sites during the process for healing the damaged corneal tissues and further there are sometimes observed reduction in the degree of transparency and a change in the refractive power of the cornea due to the presence of cellular materials thus excessively produced. The normal corneal epithelium in general comprises about 5 layers, but when the traumatic injury reaches even the stroma of cornea and it is complicatedly damaged, the corneal epithelial cells covering the stroma may sometimes run up to about 10 layers. The damaged corneal cells undergo hyperplasia and produce metabolites such as collagen and proteins to thus restore the damaged tissue. The multilayered epithelium will return to the normal structure in the future, but the refractive power and the transparency of the cornea are influenced by the transient hyperplasia and the cellular materials produced by the epithelial cells as well as the stroma cells during the damaged tissue-healing process. Moreover, a steroid drug is administered after the operation for cornea using an excimer laser, but it has been known that this is accompanied by steroid glaucoma (high intraocular pressure disease) and steroid cataract as side effects.

In the cataract surgery, there is in general performed the extra capsular cataract extraction and peripheral portions of the anterior lens capsule and the posterior lens capsule are retained. However, lens epithelial cells still remain in the lens capsule and this sometimes leads to proliferation and development of the remaining lens epithelial cells in the lens capsule and the occurrence of lenticular haze/opacity. An intraocular lens is intraocularly transplanted to correct the visual acuity, simultaneous with the cataract surgery. However, lens epithelial cells, fibrin, anterior epithelial cell of iris and phagocytes as inflammatory cells in the aqueous humor are deposited on the transplanted intraocular lens and this may sometimes affect the transparency of the intraocular lens and may result in reduction of the visual acuity of the patient after the operation. It has also been known that the lens epithelial cells are proliferated in the lens capsule over a long time period after the operation, produce cellular materials such as collagen and gradually adversely affects the visual acuity of the patient. It has been believed that the two-rank-reduction in the visual acuity is observed on about 10% of the patients having cataract surgery after one year from the operation and on about 20% of the patients after two years from the operation.

As methods for preventing cornea from becoming turbid after operations, there have conventionally been in course of studies or there have practically been applied, for instance, a method in which the lens epithelial cells are removed mechanically or by a cytotoxin which can specifically affect the epithelial cells; a method for inhibiting the outgrowth of the lens epithelial cells by devising the shape of the intraocular lens to be transplanted; and a method for inhibiting the activity of the lens epithelial cells by administering, for instance, an anti-inflammatory agent or an inhibitory agent for cellular metabolism after the operation. However, there has not yet been developed any safe and effective method.

The foregoing are examples in the field of ophthalmology, which are accompanied by several problems concerning the operation of the anterior ocular region.

DISCLOSURE OF THE INVENTION

Accordingly, a first object of the present invention is to provide an ophthalmic composition for preventing any deterioration, after operation, of the ocular optical transparency due to the hyperplasia of anterior ocular cells in the tissues damaged by an ophthalmic operation, which are in course of a healing process, and/or excess production of cellular materials by the cells.

A second object of the present invention is to provide an ophthalmic composition for controlling any hyperplasia of inflammatory cells and lens epithelial cells present in the aqueous humor during the process for healing the tissues damaged by an intraocular operation for the anterior ocular region and/or any excess production of cellular materials by the cells to thus hold the transparency of the anterior ocular region of the eye ball and the normal intraocular pressure.

A third object of the present invention is to provide an ophthalmic composition for controlling any hyperplasia of corneal epithelial cells and keratocytes during the process for healing the tissues damaged by a corneal operation and/or any excess production of cellular materials by the cells to thus hold the transparency and the normal refractive power of the cornea.

A fourth object of the present invention is to provide a method for preventing any deterioration of the optical transparency of the human anterior ocular region due to the hyperplasia of the anterior ocular cells, which are in course of the process for healing the damaged tissues, and/or excess production of materials by the cells.

A fifth object of the present invention is to provide an ophthalmic composition for preventing any deterioration of the optical transparency of the intraocular transparent bodies in the human anterior ocular region and the occurrence of high intraocular pressure disorder, due to intraocular inflammation caused by inflammatory diseases including glaucoma.

A sixth object of the present invention is to provide an ophthalmic composition for treating patients suffering from corneal degeneracy.

The inventors of this invention have conducted various studies to accomplish the foregoing objects, have found out that active vitamin D can control the cellular activity of, for instance, corneal epithelial cells, keratocytes, tissues in the anterior ocular region, and inflammatory cells and lens epithelial cells, can maintain the optical transparency, and normal refractive power of the anterior ocular region as well as the normal intraocular pressure and can prevent any reduction in the visual functions and thus have completed the present invention.

The present invention provides an ophthalmic composition for preventing any deterioration, after an ophthalmic operation, of the ocular optical transparency, high intraocular pressure disorders or defective sight caused due to hyperplasia of anterior ocular cells in the tissues damaged by the operation, which are in course of the healing process, and/or excess production of cellular materials by the cells. The composition comprises active vitamin D as an effective component.

The present invention provides an ophthalmic composition for preventing any deterioration, after an ophthalmic operation, of the optical transparency of the transparent bodies of the human eye or defective sight due to the hyperplasia of the anterior ocular cells, in the tissues damaged by the operation, which are in course of the healing process and/or excess production of cellular materials by the cells. The composition comprises active vitamin D as an effective component.

The present invention provides an ophthalmic composition for controlling any hyperplasia of inflammatory cells present in the aqueous humor and lens epithelial cells during the process for healing the tissues damaged by an intraocular operation for the anterior ocular region and/or any excess production of cellular materials by the cells to thus hold the transparency of the anterior ocular region of the eyeball as well as the normal intraocular pressure. The composition comprises active vitamin D as an effective component.

The present invention provides an ophthalmic composition for preventing any deterioration of the optical transparency of the intraocular transparent bodies in the human anterior ocular region and the occurrence of high intraocular pressure disorder, due to intraocular inflammation including glaucoma, caused by inflammatory diseases. The composition comprises active vitamin D as an effective component.

The present invention provides an ophthalmic composition for treating patients suffering from corneal degeneracy, in particular, human patients suffering from corneal degeneracy. The composition comprises active vitamin D as an effective component.

The present invention provides an ophthalmic composition for treating patients suffering from glaucoma, which comprises active vitamin D as an effective component.

The present invention provides an ophthalmic composition for preventing any change in the refractive power of the cornea, which comprises active vitamin D as an effective component.

The present invention provides an ophthalmic composition for treating the inflammation in the anterior ocular region, which comprises active vitamin D as an effective component. Examples of such inflammation of the anterior ocular region of the eyeball include glaucoma, conjunctivitis, scleritis, uveitis, iridocyclitis, choroiditis, amicrobic intraocular inflammation and bacterial endophthalmitis.

The present invention provides a method for preventing any deterioration of the optical transparency of the human anterior ocular region due to the hyperplasia of the cells, which are in course of the process for healing the damaged tissues, and/or excess production of cellular materials by the cells. The method makes use of active vitamin D as an effective component.

BEST MODE FOR CARRYING OUT THE INVENTION

The present invention provides an ophthalmic composition for controlling any hyperplasia of inflammatory cells present in the aqueous humor and lens epithelial cells during the process for healing the tissues damaged by an intraocular operation for the anterior ocular region and/or any excess production of cellular materials by the cells to thus ensure the transparency of the anterior ocular region of the eyeball and the normal intraocular pressure and the composition comprises active vitamin D as an effective component. Examples of intraocular operations for anterior ocular regions are operations for glaucoma and cataract and operations for transplantation of intraocular lenses.

The present invention provides an ophthalmic composition for controlling any hyperplasia of corneal epithelial cells and keratocytes during the process for healing the tissues damaged by a corneal operation and/or any excess production of cellular materials by the cells to thus ensure the transparency and the normal refractive power of the cornea and the composition comprises active vitamin D as an effective component. Examples of corneal operations are those which make use of a scalpel and a laser oscillator.

The present invention provides an ophthalmic composition for preventing any deterioration, after an ophthalmic operation, of the optical transparency or defective sight of the transparent bodies of the human eye due to the hyperplasia of the anterior ocular cells which are in course of the healing process of the tissues damaged by the operation and/or excess production of cellular materials by the cells and the composition comprises active vitamin D as an effective component. Examples of ocular transparent bodies are aqueous humor, intraocular lenses, lens capsule and vitreous bodies.

The ophthalmic composition of the present invention comprises active vitamin D as an effective component. Specific examples of active vitamin D's are ergocalciferol derivatives, ergocalciferol analogues, cholecalciferol derivatives, cholecalciferol analogues and hydrophilic active vitamin D analogues each carrying hydrophilic groups on the side chains. The active vitamin D may be naturally occurring ones or synthetic active vitamin D analogues.

Particularly preferred in the present invention are monohydroxy derivatives of vitamin D each of which carries a hydroxy group on one or both of the C1 position on the sterol A ring and the C25 position on the side chain; and dihydroxy derivatives in which the C1 and C24 positions or C1 and C25 positions are hydroxylated. Preferred examples thereof further include calcitriol ($\alpha$,25-dihydroxy vitamin D), 1$\alpha$,24-dihydroxy vitamin D, alpha-calcidol (1$\alpha$-monohydroxy vitamin D), calcifedol (25-monohydroxy vitamin D), 1$\alpha$,24,25-trihydroxy vitamin D, 1$\alpha$,25,26-trihydroxy vitamin D, 1$\beta$,25-dihydroxy vitamin D, 24-homo-1$\alpha$,25-dihydroxy vitamin D, 26-homo-1$\alpha$,25-dihydroxy vitamin D, OCT (22-oxacalcitriol) and calcipotriol. Among these, a naturally occurring cholecalciferol derivative, i.e., calcitriol (1$\alpha$,25-dihydroxy vitamin D) is particularly preferred because it is free of any cytotoxicity and is highly active.

It has been recognized that the smaller the molecular weight and the higher the degree of hydrophobicity, the higher the permeability of the drug through the cornea. Calcitriol as a cholecalciferol derivative has a molecular weight of 416.64 dalton, synthetic alpha calcidol has a molecular weight of 400.64 dalton and these active vitamin D's are excellent in the permeability through cornea.

It has also been known that dihydrotachysterol (DHT) as an active vitamin D analogue shows affinity for active vitamin D receptors present in cells and that it would have an effect similar to that observed for the active vitamin D. Thus the analogue is included in the "active vitamin D" used in the present invention.

The ophthalmic composition of the present invention is in general used in the form of an eye drop. The active vitamin D used as the effective component in the present invention is oil-soluble and it is preferably converted into an aqueous solution by diluting it with a solvent or diluent such as ethanol and finally diluting with the ophthalmic physiological buffer or converted into the usual ophthalmic solution in oil by dissolving a diluent prepared by diluting active vitamin D with, for instance, ethanol in oils and fats (e.g., sesame oil).

The ophthalmic composition of the present invention may likewise be used in the dosage forms administered per oral or parenteral routes such as injections, powdered drugs, tablets, capsules, powders and aerosols. Alternatively, it is also possible to encapsulate active vitamin D in an ophthalmic drug-delivery system such as liposome, microsphere, gel-like protein, collagen, soft contact lenses for treatment or intraocular lenses or to adhere such vitamin to the drug-delivery system to thus directly administer or deliver active vitamin D to damaged tissues or sites in the form of an ophthalmic treating agent.

The lacrimal fluid is viscous and oil-soluble. Therefore, active vitamin D may preferably be admixed with at least one viscous base or oil base selected from the group consisting of, for instance, polyvinyl alcohol, methyl cellulose, hyaluronic acid, chondroitin sulfuric acid, collagen and oils and fats to thus give a viscous ophthalmic solution which can be used as an eye drop or an agent directly administered into the aqueous humor.

It would be sufficient, in the present invention, that active vitamin D is administered in an amount ranging from 0.1 to 10 ng/dose/day for local administration. This corresponds to 1/5000 to 1/50 time the amount required for the usual administration through oral route and accordingly, there would almost be no systemic side effect.

When orally administering a large amount of the conventional vitamin D-containing pharmaceutical preparation, there is observed hypervitaminosis D in which the calcium and phosphoric acid contents in the blood increase and which is accompanied by the calcification of soft tissues such as kidney, arterial blood vessel, smooth muscles and lung. When the active vitamin D-containing ophthalmic composition of the present invention is administered in the form of an eye drop, it would take effect through local administration even when it is administered in an amount smaller than that conventionally used, for instance, in an amount of not more than 1/50 time that required for the oral administration and there would almost be no side effect unlike the conventional technique even if a certain amount of active vitamin D penetrates into the blood through the ocular mucous membrane.

Oral administration of active vitamin D also shows an effect of preventing the deterioration of the optical transparency of human eyes due to the hyperplasia of cells in damaged tissue-healing process and/or the excess production of cellular materials by the cells. However, active vitamin D must be administered in a large amount in order to achieve the same effect observed when it is locally administered to the eye. For this reason, the ophthalmic composition of the present invention is most preferably administered in the form of an eye drop.

In the present invention, an active vitamin D-containing ophthalmic composition is used for preventing the deterioration of he optical transparency of the human anterior ocular region due to the hyperplasia of cells during damaged tissue-healing process and/or the excess production of cellular materials such as collagen and proteins by the cells.

The vitamin D orally taken is converted into active vitamin D in the liver and/or kidney. It is known that, in the skin, 7-dehydrocholesterol is converted into previtamin D by the irradiation with ultraviolet rays in the sunlight and thereafter converted into active vitamin D in the liver and/or kidney.

The ophthalmic composition of the present invention is, for instance, used in the following manner.

When the transparency of the anterior ocular region of the human eyeball is impaired due to proliferation of, for instance, corneal epithelial cells, keratocytes, and inflammatory cells present in the aqueous humor and lens epithelial cells for the healing of damaged tissues and/or the production of cellular materials by the cells, the active vitamin D-containing ophthalmic solution of the present invention can be administered in the form of an eye drop to control the activity of these anterior ocular cells and to thus hold or ensure the desired transparency, normal refractive power and normal intraocular pressure.

Moreover, the active vitamin D-containing eye drop of the present invention is administered to a patient who has been subjected to a cataract operation immediately after the operation so that active vitamin D can permeate even into the posterior chamber from the anterior ocular region of the eye to control the activity of the lens epithelial cells and to thus prevent any reduction of the visual acuity due to the opacification of the lens capsule. Moreover, the administration of the active vitamin D-containing composition of the present invention permits the inhibition of the opacification of the transplanted intraocular lens surface due to the deposition of phagocytes present in the aqueous humor on the surface of the lens. The cataract surgery may sometimes be accompanied by accidental breakage of the capsule and inflammatory cells are penetrate into the vitreous body from the posterior chamber after the operation to thus cause opacification of the vitreous body. If administering, after the operation, the active vitamin D-containing composition of the present invention in the form of an eye drop, however, any such opacification of the vitreous body can be prevented.

In addition, the active vitamin D-containing eye drop of the present invention is administered to a patient who has been subjected to operation for glaucoma immediately after the operation so that active vitamin D can permeate even into the tissues of the anterior chamber gonion to control the cellular activity of tissues such as the Schlemm's canal of the anterior chamber gonion, to thus suppress the hyperplasia of the anterior chamber gonion near the operated site and/or excess production of cellular materials and to prevent the recurrence of glaucoma.

The active vitamin D-containing eye drop of the present invention would show more higher cell activity-inhibitory effect if the eye drop is administered to a patient several days before the ophthalmic operation.

Furthermore, the active vitamin D-containing ophthalmic composition of the present invention can likewise be used for the treatment of the corneal degeneracy. Active vitamin D may correct any abnormal metabolism of the keratocytes to thus allow the keratocytes to synthesize proteins normally and to thus allow the keratocytes to undergo normal differentiation-induction.

The active vitamin D-containing ophthalmic composition of the present invention can be administered to a patient who has been subjected to an operation for cornea with a scalpel or a laser in the form of an eye drop to inhibit the hyperplasia of the corneal epithelial cells and keratocytes and any excess production of cellular materials such as collagen, to control the tugging of the wound due to the scaring, to prevent any change of the refractive power of the cornea and any turbidity of the cornea and to thus prevent any reduction of the visual acuity. The administration of the active vitamin D-containing ophthalmic solution of the present invention can control the cellular activity during the process for healing the damaged tissues and can likewise prevent any deterioration of the transparency of the human anterior ocular region due to the hyperplasia of the intraocular cells during the damaged tissue-healing process and the excess production of cellular materials.

In the patient who has been subjected to the keratectomy using an excimer laser, corneal epithelial cells are regenerated on the stroma after the keratectomy and the regeneration is completed within several days. The epithelial cells are thus regenerated, but there are observed epithelial hyperplasia and rise in epithelium and keratocyte cell activity at the periphery of the site from which the cornea is removed by the operation with an excimer laser and at sites from which the keratocytes are complicatedly removed. Reduction of visual acuity may be caused at these sites because of a corneal refractive power change and turbidity thereof due to cellular materials of the epithelial cells and keratocytes. A steroid drug has mainly been used to prevent the occurrence of these phenomena, but the administration thereof may cause, as side effects, steroid-induced glaucoma and steroid-induced cataract and accordingly, there has been a tendency of avoiding the use of any steroid-containing drug. Thus, if administering the ophthalmic composition of the present invention to a patient who has been subjected to keratectomy with an excimer laser in the form of an eye drop, the active vitamin D as the effective component thereof can inhibit the hyperplasia of the epithelial cells and the activity of the keratocytes and can in turn prevent the reduction of visual acuity due to any refractive power change and turbidity of the cornea.

As has been discussed above, Dr. Ohashi et al. in Osaka University studied the inhibitory effect of vitamin $D_3$ against the expression of MHC class antigens in order to suppress any rejection observed during the keratoplasty and suggest that vitamin $D_3$ may serve to control the rejection of the transplantation of cornea. However, the present invention is completely independent of the rejection observed during the keratoplasty and is based on such a finding that active vitamin D can maintain the transparency of the cornea and/or stabilize the refractive power thereof.

Japanese Un-Examined Patent Publication No. Hei 3-24016 discloses that active vitamin $D_3$ is effective for the treatment of the proliferative retinopathy. However, the present invention is independent of the proliferative retinopathy of the eyeground and is based on such a finding that active vitamin $D_3$ has an anti-inflammatory effect on the inflammatory cells in the anterior intraocular region and can maintain the optical transparency of the anterior ocular region during the process for healing damaged tissues after the ophthalmic operations and/or can stabilize the refractive power thereof.

Japanese Examined Patent Publication No. Hei 4-43887 discloses that active vitamin $D_3$ is effective for the treatment of cataract while making use of the hypercalcemic action of active vitamin $D_3$. However, the present invention is independent of the treatment of patients suffering from cataract while making use of the hypercalcemic action of active vitamin $D_3$ and is based on such a finding that active vitamin $D_3$ has an anti-inflammatory effect on the inflammatory cells in the anterior intraocular region and can maintain the optical transparency of the anterior ocular region during the process for healing damaged tissues after the ophthalmic operations and/or can stabilize the refractive power thereof.

The ophthalmic composition of the present invention is effective for inhibiting or suppressing the intraocular inflammation of patients and the activity of cells in course of the healing process of damaged tissues after operations.

The present invention is based on such a finding that the local administration of active vitamin D to the eye permits the maintenance of desired transparency, normal refractive power and normal intraocular pressure. On the other hand, it has been known that the vitamin D taken from foods is converted into active vitamin D in the kidney and liver. For this reason, the oral administration of non-active form of vitamin D may have the same ocular transparency-maintaining effect observed for active vitamin D. However, sufficient conversion of non-active form of vitamin D into active vitamin D cannot be expected in patients who also suffer from kidney and/or liver deficiencies and therefore, the administration of active vitamin D is effective for achieving the ocular transparency-maintaining effect.

According to the method of locally administering the ophthalmic solution of the present invention to the eye, it would be recognized that the active vitamin D binds to the vitamin D receptor to form a complex and that the complex is incorporated into cell nuclei to affect the DNA and to thus control the activity of the cells, but active vitamin D does not adversely affect the normal ocular cells unless it is administered in an extremely excess amount since it does not show any cytotoxicity.

The vitamin C deficiency results in reduction in the number of vitamin D receptors and thus adversely affects the incorporation of active vitamin D into the nuclei. Accordingly, the presence of vitamin C is quite important and in particular, patients desirably take a sufficient amount of vitamin C when using the ophthalmic composition of the present invention. Therefore, the ophthalmic composition of the present invention which is further admixed with vitamin C would show further improved effect of active vitamin D and thus the use thereof is preferred. Vitamin C is preferably incorporated into the composition in an amount ranging from about 1 to 100 mg/ml.

It would be difficult to deliver active vitamin D even to the eyeground according to the method for administering the ophthalmic composition of the present invention in the form of an eye drop and thus it would be more effective to use the method simultaneously with the oral administration of vitamin D when the posterior ocular region of a patient is to be treated with active vitamin D.

The composition of the present invention may be administered, in the form of an eye drop, to a patient, whose anterior ocular region has been operated, over a long period of time after the operation, but as has been discussed above, it is also possible to encapsulate active vitamin D in an ophthalmic drug-delivery system such as liposome, microsphere, gel-like protein, collagen, soft contact lenses for an ophthalmic treatment or intraocular lenses or to adhere such vitamin to the drug-delivery system to thus directly administer active vitamin D to damaged tissues or sites in the form of an agent for ophthalmic treatments, which may have a sustained release effect of the drug.

Moreover, active vitamin D is inactivated when it is oxidized and therefore, it would be desirable to use a container for storage or an antioxidant when storing it in the form of an ophthalmic solution or when administering it while expecting the sustained release effect thereof.

As has been described above, the usual vitamin D is converted into active vitamin D in liver and kidney and accordingly, the intended effect of the present invention cannot be achieved even if the usual vitamin D is locally administered to the eye.

In respect of safety of active vitamin D, Enjyo et al. carried out toxicity tests and irritability tests for a synthetic 1α,24-dihydroxycholecalciferol-containing ointment using the skin and ocular mucous membrane of rabbit to thus confirm the safety thereof ("Toxicity Investigation of TY-02" in YAKURI TO CHIRYO (Pharmacological Action and Treatment), Vol. 17, No. 10, October, 1989).

The present invention will hereinafter be explained in more detail with reference to the following Preparation Examples and Test Examples.

PREPARATION EXAMPLE 1

An active vitamin D stock solution (content of 1α-monohydroxy vitamin D: 50 mg/ml) was diluted 1000 times with ethanol and the resulting dilute solution was further diluted 100 times with an ophthalmic physiological buffer solution to give an ophthalmic composition having a 1α-monohydroxy vitamin D concentration of 0.5 μg/ml.

PREPARATION EXAMPLE 2

A calcitriol stock solution (content of 1α,25-dihydroxy vitamin D: 50mg/ml) was diluted 1000 times with ethanol and the resulting dilute solution was further diluted 100 times with an ophthalmic oil base comprising purified sesame oil to give an ophthalmic composition having a calcitriol concentration of 0.5 μg/ml.

PREPARATION EXAMPLE 3

Vitamin C (phosphoric acid salt of L-ascorbic acid, 60 mg) was mixed with and dissolved in 10 ml of the ophthalmic composition prepared in Preparation Example 1 to give an ophthalmic composition consisting of a mixed solution having a vitamin C concentration of 6 mg/ml and an active vitamin D concentration of 0.5 μg/ml.

TEST EXAMPLES

Active vitamin D was inspected for the efficacy and safety when a patient suffered from an iatrogenic corneal trauma by an ophthalmic operation in Test Example 1; active vitamin D was inspected for the safety and efficacy, in the anterior intraocular region, for preventing any opacification of the lens capsule and any opacification of the aqueous humor and intraocular lenses, in Test Example 2; and active vitamin D was inspected for the efficacy and safety during the process for healing the wound when the cornea had been damaged, in Test Example 3. In these experiments, rabbits were used.

TEST EXAMPLE 1

In this test, 6 Japan white rabbits each weighing 2 kg were used. After anesthetizing each animal by intramuscularly injecting an analgesic-anesthetic at the femoral regions thereof and by simultaneously dropping local anesthetic in the eyes, a laser beam was focused on the corneal center of the right eye using an excimer laser oscillator (available from Summit Technology Co. U.S.). The laser beam irradiation was carried out according to the surface-incision mode (PTK), i.e., at an energy density of 165 mj/cm$^2$, a rate of incision to a depth of 0.25 μm/pulse, an incised surface diameter of 4.5 mm and a pulse number of 300.

After the laser beam irradiation, an eye drop and an ointment containing an antibiotic agent were administered to the eye. Three (Group A) out of these six animals were treated by dropping, in the right eye, an active vitamin D-containing solution (1α-monohydroxy vitamin D: 0.01 μg/drop or 0.5 μg/ml; an alpha calcidol solution) in a rate of one drop (0.02 ml)/dose/day, starting from 24 hours after the laser beam irradiation. On the other hand, the remaining three (Group B) out of these six animals constituted a control group and were treated in the same manner by dropping, in the right eye, an ophthalmic buffer solution BSS at a rate of one drop/dose/day.

After 4, 7 and 12 days from the laser beam irradiation, the right eyes of animals in Group A and Group B (one animal each) were observed under a slit lamp microscope, followed by slaughtering one animal in each Group and then enucleation of the eyeballs. The cornea was removed from the sclerocornea of each eyeball, followed by fixing through immersion in a Carnoa's solution for 4 hours, dehydration in dry ethanol, paraffin-embedded to form a corneal slice with a thickness of 4 μm, removing paraffin by xylol, carrying out the hematoxylin-eosin staining and/or PAS staining and observation of the corneal slice under a light microscope.

As a result of the observation under the slit lamp microscope, there were observed, for the right eyes of the animals in Group B, stronger opacity at the peripheral edge of the laser-irradiated site and turbidity over the whole irradiated area. On the other hand, there was observed, for the right eyes of the animals in Group A, quite slight opacity at the peripheral edge of the laser-irradiated site and thus, it is clear that the result is quite different from that observed for the animals in Group B. There was also observed distinct difference between the animals in Groups A and B during the experimental period, even by the visual observation.

As a result of the observation of the sliced cornea under a light microscope, there was observed, for the right eye of the animals in Group B, piling up growth of the corneal epithelial cells at the periphery of the incised site in such a manner that the corneal epithelial cells initially ran up to 10 layers at the periphery and inwardly reduced to about 5 to 8 layers. On the other hand, there was not observed such tendency as piling up growth for the right eyes of the animals in Group A.

In a test which made use of an anti-collagen type III, goat monoclonal antibody, the higher the piling up growth tendency of the corneal epithelial cells and the greater the number of accumulated keratocytes, the greater the amount of collagen type III deposited as a cellular metabolite. The strongly opacified portion at the periphery of the laser-irradiated corneal area on the right eye of Group B would suggest the possibility of undergoing cicatrization resulting the tissue-tugging, as the tissue fibrosis following the accumulation of type III collagen proceed. This in turn becomes a cause of a refractive power change of the cornea.

TEST EXAMPLE 2

In this test, three Japan white house rabbits each weighing 2 kg were used. After anesthetizing each animal by intramuscularly injecting an analgesic-anesthetic at the femoral regions thereof and by simultaneously dropping a local anesthetic in the eyes, the sclerocornea of each animal was dissected over a length of 3.5 mm, followed by excising a circular piece of the arterior capsule at a diameter of about 5 mm from the lens capsule under perfusion of the ophthalmic buffer solution BSS, removal of the lens nuclei and the cortex by the ultrasonic emulsification and aspiration technique, swelling the lens capsule by injecting a viscoelastic substance, then widening the incised port of the sclerocornea to about 7 mm and transplantation, into the lens capsule, of a poly(methyl methacrylate) intraocular lens provided with an optical part having a diameter of 6 mm. After the removal of the viscoelastic substance under vacuum suction, the incised wound of the sclerocornea was sutured with three stitches using a 9-0 nylon suture to thus complete the operation. After the completion of the operation, an eye drop and an ointment containing an antibiotic agent were administered to the conjunctiva. The right eyes of these three animals were subjected to the ultrasonic emulsification and aspiration technique and the transplantation of an intraocular lens.

One (A) out of these three animals was treated with a calcitriol solution in a rate of 1 to 2 drops/dose/day. The calcitriol solution used was prepared by dissolving and diluting calcitriol (1α,25-dihydroxy vitamin D) in ethanol and then further diluting (1:100) the resulting dilute solution, to a calcitriol concentration of 0.5 μg/ml, with an ophthalmic oil base consisting of purified sesame oil. One (B) out of the three animals was treated by orally administering the calcitriol solution in a rate of 1 ml/dose/day using a dropping pipette. The remaining one (C) out of the three animals was treated by dropping ophthalmic purified sesame oil free of any calcitriol in the right eye in a rate of 1 to 2 drops/dose/day. After the mydriasis at 1, 4, 7, 14 and 28 days from the operation, the lens capsule, aqueous humor and intraocular lens for each animal were inspected for the turbidity through the observation under a slit lamp microscope.

Fibrin was abundantly deposited in the anterior chamber of the right eye of the animal C on the day subsequent to the operation, but it was gradually disappeared and then completely disappeared on approximately 4th day from the operation. The fibrin deposition in the anterior chamber was also observed for the animals A and B, but the extent of the deposition was very low as compared with that observed for the animal C.

In contrast with the disappearance of the deposited fibrin, it was observed that the lens capsule of the right eye of the animal C was began to wrinkle after approximately 4 days from the operation and that the anterior capsule became turbid and began to shrink after about 28 days from the operation. There was observed accumulation of the lens epithelial cells or a metabolite which would seem to be collagen at the periphery of the incised anterior capsule as well as the periphery and supporting arm of the intraocular lens. There were observed the presence of cell-like deposits on the surface of the intraocular lens. On the other hand, there were observed, for the right eye of the animal A, only slight wrinkling of the anterior capsule and opacity of the periphery thereof even after 7 days from the operation and the anterior capsule maintained desired transparency. There were observed, for the right eyes of the both animals A and B, slight opacity and wrinkling of the anterior capsule after 28 days from the operation, but the transparency observed for the animal A was better than that observed for the animal B. All of the eyes examined did not cause any posterior synechia.

In both Test Examples 1 and 2, there was not observed any side effect such as the ones caused by the vitamin D treatment, bleeding, fibrin-deposition, corneal haze/opacity and/or intraocular inflammation. It was confirmed that the local administration of active vitamin D to the eye according to the present invention permits the control of the activity of cells which are in the inflamed conditions and during the process for healing damaged tissues and the control of the excess production of cellular materials.

TEST EXAMPLE 3

In this test, 8 Japan white rabbits each weighing 2 kg were used. A laser beam was focused on the corneal center of the right eye of each animal using an excimer laser oscillator (available from Summit Technology Co. U.S.) under anesthesia. The laser beam irradiation was carried out according to the surface-incision mode (PTK), i.e., at an energy density of 165 mj/cm$^2$, a rate of incision to a depth of 0.25 $\mu$m/pulse, a diameter of the incised circular area of 4.5 mm and an irradiated pulse number of 300.

These 8 test animals which had been irradiated with the laser beam were, at random, divided into two groups each comprising 4 animals, one of which constituted a drug-administered group and the other of which constituted a control group. In addition, an eye drop containing an antibiotic agent was administered by dropping it in the eyes on the day of less irradiation and the day subsequent thereto.

After 24 hours from the laser irradiation, the drug-administered group and the control group were treated by dropping, in the right eye, a $10^{-7}\%$ active vitamin D-containing solution [22-oxa-1$\alpha$,25-dihydroxy vitamin D$_3$: OCT (available from Chugai Pharmaceutical Co., Ltd.)] and the OCT solvent base, respectively, at 20 $\mu$l/dose and 3 times/day over 14 days. After 7 and 15 days from the irradiation, the extent of the turbidity of each cornea was evaluated on the basis of the findings for the 8 animals observed under a slit lamp microscope. More specifically, the degree of turbidity was rated according to the criteria which extend from 0 (there was not observed any corneal turbidity at the peripheral and central portions of the laser-irradiated cornea) to 4 (there was observed complete opacification of the laser-irradiated cornea). Each average of four animals is as follows:

| Control Group | 3.5 |
|---|---|
| Drug-Administered Group | 2.0 |

In the control group, there was observed complete opacification of the whole area which had been irradiated with a laser beam and the degree thereof was intensive at the periphery of the area and slightly weak at the central portion thereof. Contrary to this, the laser beam-irradiated area also became turbid in the drug-administered group, but the degree thereof was found to be about ½ time that observed for the control group, which was judged to be significantly low.

The test results obtained in Test Examples 1 to 3 clearly indicate that the ophthalmic composition of the present invention is effective and safe for the human body.

The dropping, in the eye, of the active vitamin D-containing composition of the present invention over a long time period permits the inhibition of any deterioration of the optical transparency of the anterior ocular region or the occurrence of high intraocular pressure disease or the defective sight due to the hyperplasia of the anterior ocular cells during damaged tissue-healing process and/or excess production of cellular materials and can in turn prevent any reduction of the visual acuity. This would accordingly permit the elimination of the operation for incising the posterior or anterior lens capsule by a YAG laser.

If the active vitamin D-containing composition of the present invention is administered to a patient suffering from, for instance, an endophthalmitis, glaucoma or corneal degeneracy, the composition permits the complete treatment of these diseases.

The dropping, in the eye, of the active vitamin D-containing composition of the present invention after the operation for the transplantation of an intraocular lens allows the inhibition of the opacification of the intraocular lens surface and the vitreous body and the prevention of any reduction of the visual acuity.

The dropping, in the eye, of the active vitamin D-containing composition of the present invention after the operation of the cornea with a scalpel or a laser allows the prevention of any opacification of the corneal subepithelial region and any reduction of the visual acuity.

The dropping, in the eye, of the active vitamin D-containing composition of the present invention after the operation of the cornea with a scalpel or a laser allows the prevention of the transient hyperplasia of the corneal epithelial cells and any excess production of metabolites by the corneal epithelial cells and keratocytes as well as any change of the corneal refractive power after the operation and also permits the elimination of any side effect which has been a serious problem encountered when a steroid-containing drug is dropped in the eye after the operation for the cornea with a scalpel or a laser.

The local administration of the active vitamin D-containing composition of the present invention to the anterior ocular region have almost no possibility of causing hypervitaminosis D which may be caused when taking a large amount of the usual vitamin D-containing drug, since the composition has a low vitamin D concentration.

The intended effect of maintaining the transparency of the ocular transparent bodies can be expected when the active vitamin D-containing composition of the present invention is locally and/or systemically administered through the oral route to the patient whose functions of the liver and the kidney are impaired.

The local administration of the active vitamin D-containing composition of the present invention to the anterior ocular region is completely safe since active vitamin D does not have any cytotoxicity.

A more improved effect can be expected when using the ophthalmic composition of the present invention which further comprises vitamin C incorporated therein.

What is claimed is:

1. A method for an ophthalmic treatment, comprising administering an ophthalmic composition to an eye, said composition comprising active vitamin D in combination with vitamin C; wherein said composition is administered in an amount sufficient to prevent deterioration of:
   (i) the optical transparency, observed after an ophthalmic operation, in the course of the healing process;
   (ii) occurrence of high intraocular pressure disease, observed after an ophthalmic operation, in the course of the healing process;
   (iii) defective sight observed after an ophthalmic operation, in the course of the healing process;
   (iv) the optical transparency or defective sight of a transparent body of a human eye, observed after an ophthalmic operation of the anterior ocular region of the human eye, due to the hyperplasia of the anterior ocular cells which are in the healing process of the tissue damaged by the operation and/or excess production of cellular materials;
   (v) the optical transparency of intraocular transparent bodies due to intraocular inflammation caused by an inflammatory disease in the anterior ocular region of human eyeball; or
   (vi) a high intraocular pressure disease due to intraocular inflammation caused by an inflammatory disease in the anterior ocular region of the human eyeball; or
in an amount sufficient to control:
   (vii) any hyperplasia of inflammatory cells present in the aqueous humor and lens epithelial cells during healing of the tissues damaged by an ophthalmic operation for the anterior ocular region and/or any excess production of cellular materials to maintain the transparency of the anterior ocular region of the eyeball and the normal intraocular pressure; or
   (viii) hyperplasia of corneal epithelial cells and keratocytes during healing of the tissue damaged by an ophthalmic operation for cornea and/or excess production of cellular material to maintain the optical transparency and normal refractive power of the cornea.

2. The method of claim 1, wherein the transparent body is at least one member selected from the group consisting of aqueous humor, intraocular lens, lens capsule and vitreous body.

3. The method of claim 1, wherein the ophthalmic operation for the anterior ocular region is at least one member selected from the group consisting of an operation for glaucoma, an operation for cataract and an operation for transplantation of an intraocular lens.

4. The method of claim 1, wherein the ophthalmic operation for cornea is one carried out using a scalpel or a laser.

5. A method for treating a human corneal degeneracy, comprising administering an ophthalmic composition, in a sufficient amount to treat said degeneracy, said composition comprising active vitamin D in combination with vitamin C.

6. A method for treating glaucoma, comprising administering an ophthalmic composition, in a sufficient amount to treat said glaucoma, said composition comprising active vitamin D in combination with vitamin C.

7. A method for preventing a change in the refractive power of the cornea of eyeballs, comprising administering an ophthalmic composition, in a sufficient amount to prevent said change, said composition comprising active vitamin D in combination with vitamin C.

8. A method for treating inflammation in the anterior ocular region of the eyeball, comprising administering an ophthalmic composition, in a sufficient amount to treat said inflamation, said comprising active vitamin D in combination with vitamin C.

9. The method of claim 8, wherein the inflammation in the anterior ocular region of the eyeball is at least one member selected from the group consisting of glaucoma, conjunctivitis, scleritis, uveitis, iridocyclitis, choroiditis, amicrobic intraocular inflammation and bacterial endophthalmitis.

10. The method of claim 1, wherein the active vitamin D is active vitamin D which carries a hydroxy group on one or both of the C1 position on the sterol A ring of the vitamin D and the C25 position on the side chain thereof.

11. The method of claim 10, wherein said active vitamin D is selected from the group consisting of calcitriol (1α,25-dihydroxy vitamin D), 1α,24-dihydroxy vitamin D, alpha-calcidol (1α-monohydroxy vitamin D), calcifedol (25-monohydroxy vitamin D), 1α,24,25-trihydroxy vitamin D, 1α,25,26-trihydroxy vitamin D, 1β,25-dihydroxy vitamin D, 24-homo-1α,25-dihydroxy vitamin D, 26-homo-1α,25-dihydroxy vitamin D, OCT (22-oxacalcitriol) and calcipotriol.

12. The method of claim 1, wherein the active vitamin D is dihydrotachysterol.

13. The method of claim 1, wherein the ophthalmic composition is in a dosage form to be orally administered.

14. The method of claim 1, wherein the ophthalmic composition is in a dosage form to be parenterally administered.

* * * * *